(12) United States Patent
Nazarifar et al.

(10) Patent No.: US 11,779,694 B2
(45) Date of Patent: Oct. 10, 2023

(54) SYSTEMS AND METHODS FOR PROPORTIONAL PRESSURE AND VACUUM CONTROL IN SURGICAL SYSTEM

(71) Applicant: JOHNSON & JOHNSON SURGICAL VISION, INC., Santa Ana, CA (US)

(72) Inventors: Nader Nazarifar, Laguna Niguel, CA (US); Deep Mehta, Irvine, CA (US); Lauren Hickey, Irvine, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 995 days.

(21) Appl. No.: 16/393,856

(22) Filed: Apr. 24, 2019

(65) Prior Publication Data

US 2020/0337900 A1 Oct. 29, 2020

(51) Int. Cl.
*A61M 3/02* (2006.01)
*A61F 9/007* (2006.01)
(Continued)

(52) U.S. Cl.
CPC ..... *A61M 3/0216* (2014.02); *A61B 17/320068* (2013.01); *A61F 9/00745* (2013.01);
(Continued)

(58) Field of Classification Search
CPC ......... A61F 9/00754; A61F 2009/0087; A61B 17/320068; A61B 2017/00199;
(Continued)

(56) References Cited

U.S. PATENT DOCUMENTS 6,290,690 B1 * 9/2001 Huculak ............. A61M 1/0058
604/521
2010/0030134 A1 * 2/2010 Fitzgerald ............... A61M 1/77
604/35
(Continued)

FOREIGN PATENT DOCUMENTS

| EP | 1302185 B1 | 2/2004 |
|---|---|---|
| EP | 3295906 A1 | 3/2018 |
| WO | 2004108189 A2 | 12/2004 |

OTHER PUBLICATIONS

International Search Report for Application No. PCT/IB2020/053633, dated Jul. 2, 2020, 2 pages.

*Primary Examiner* — Theodore J Stigell
(74) *Attorney, Agent, or Firm* — Johnson & Johnson Surgical Vision, Inc.

(57) ABSTRACT

A pneumatic cross-connect proportional valve provides the capability to calibrate pressure and vacuum sensors in a surgical cassette associated with a surgical console. Calibration of non-invasive pressure and vacuum sensors in a cassette by utilizing a proportional cross-connect to pressurize the lines with set pressure or vacuum the lines with set vacuum and measure the response of respective sensors in the cassette. The use of proportional pressure may be used along with other clearing methods to clear material clogging the aspiration channel pathways and tubing of the surgical system. Utilize the cross-connect functionality to more rapidly pressurize the aspiration line upon detection or prediction of a post occlusion surge, thereby reducing the pressure difference between the surgical field, the eye chamber, and aspiration line which may prevent, for example, a surge of fluid out of the anterior chamber of the eye.

19 Claims, 4 Drawing Sheets

(51) Int. Cl.
  *A61B 17/32* (2006.01)
  *A61M 1/00* (2006.01)
  *A61B 17/00* (2006.01)

(52) U.S. Cl.
  CPC .............. *A61M 1/74* (2021.05); *A61M 1/742* (2021.05); *A61M 1/774* (2021.05); *A61B 2017/00199* (2013.01); *A61B 2017/00973* (2013.01); *A61B 2017/32007* (2017.08); *A61B 2017/320084* (2013.01); *A61F 9/00754* (2013.01); *A61M 2210/0612* (2013.01)

(58) Field of Classification Search
  CPC ........... A61B 2017/00973; A61B 2017/32007; A61B 2017/320084; A61M 1/74; A61M 1/774; A61M 2210/0612; A61M 1/742; A61M 3/0216; A61M 2205/128; A61M 1/72; A61M 3/0201
  See application file for complete search history.

(56) References Cited

U.S. PATENT DOCUMENTS

| | | | |
|---|---|---|---|
| 2010/0280439 A1* | 11/2010 | Kuebler | A61M 1/74 604/35 |
| 2013/0150782 A1 | 6/2013 | Sorensen et al. | |
| 2016/0166742 A1 | 6/2016 | Layser et al. | |
| 2018/0338861 A1 | 11/2018 | Hallen | |
| 2019/0099529 A1 | 4/2019 | Mehta et al. | |

* cited by examiner

SYSTEMS AND METHODS FOR PROPORTIONAL PRESSURE AND VACUUM CONTROL IN SURGICAL SYSTEM

FIELD OF THE INVENTION

The present invention relates to phacoemulsification surgical systems, and, more particularly, a phacoemulsification surgical system comprising a pneumatic cross-connect proportional valve between pressure and vacuum systems.

BACKGROUND OF THE INVENTION

Cataracts affect more than 22 million Americans age 40 and older. And as the U.S. population ages, more than 30 million Americans are expected to have cataracts by the year 2020. Cataract surgery entails the removal of a lens of an eye that has developed clouding of the eye's natural lens, or opacification. As a result of opacification, light is unable to travel to the retina, thereby causing vision loss. Once vision becomes seriously impaired, cataract surgery is a viable option with a high level of success. During cataract surgery, a surgeon replaces the clouded lens with an intraocular lens (IOL).

Certain surgical procedures, such as phacoemulsification surgery, have been successfully employed in the treatment of certain ocular problems, such as cataracts. Phacoemulsification surgery utilizes a small corneal incision to insert the tip of at least one phacoemulsification handheld surgical implement, or handpiece, through the corneal incision. The handpiece includes a needle which is ultrasonically driven once placed within the incision to emulsify the eye lens, or to break the cataract into small pieces. The broken cataract pieces or emulsified eye lens may subsequently be removed using the same handpiece, or another handpiece, in a controlled manner. The surgeon may then insert a lens implant into the eye through the incision. The incision is allowed to heal, and the result for the patient is typically significantly improved eyesight.

Currently during cataract surgery, a majority of phacoemulsification platforms provide three primary states for fluidics and phaco control: irrigation, aspiration and ultrasound with respective operative foot pedal activation zones. The foot pedal treadle position 1, which correlates to irrigation only mode of the fluidics control and in which irrigation valve, is opened to allow either gravity or pressurized irrigation flow to reach the chamber via a sleeve at distal end. Foot pedal treadle position 2, which correlates to irrigation/aspiration mode of the fluidics control, in which both irrigation and aspiration valves are opened to allow both fluid and Cataract particles to be aspirated out of the chamber while chamber pressure is maintained using the irrigation flow. Foot pedal treadle position 3, which correlates to irrigation/aspiration/ultrasound mode of fluidics and phaco control, in which ultrasound energy is applied to emulsify the cataract particle whilst emulsified particles are being aspirated out of the chamber to a waste bag in the cassette.

In flow mode aspiration, the fluidics control provides a capability to gradually increase or decrease aspiration flow by traversing the foot pedal treadle in zone 2. In vacuum mode aspiration, the fluidics control provides a capability to gradually increase or decrease aspiration vacuum by traversing the foot pedal in zone 2. In both aspiration modes, the fluidics control can relieve vacuum in the aspiration line when the foot pedal is traversed from zone 2 to zone 1; in other words, when the fluidics controls is switched from irrigation/aspiration to irrigation only. When the foot pedal treadle is traversed from zone 1 (irrigation only) to zone 0 (idle), the fluidics control pressurizes the aspiration line to a set point. By relieving vacuum and applying pressure in the aspiration line, the fluidics control pushes fluid out of the aspiration line into the chamber thus clearing any obstructing particles or eye tissue occluding the tip of the surgical instrument. Current phacoemulsification systems generate pressure in the aspiration line by using a peristaltic pump or column height of the fluid to allow irrigation head height to pressurize the aspiration line.

BRIEF SUMMARY OF THE INVENTION

In an embodiment of the present invention, the use of a cross-connect valve may provide the capability to calibrate pressure and vacuum sensors in a surgical cassette associated with a surgical console, for example. The present invention may support calibration of non-invasive pressure and vacuum sensor in the cassette by utilizing the proportional cross-connect to pressurize the lines with set pressure or vacuum the lines with set vacuum and measure the response of respective sensors in the cassette. This may require, for example, that irrigation and aspiration lines are at least partially connected, for example.

The present invention may also provide for the clearing of obstructions in the aspiration channel fluid pathways by applying proportional pressure. The use of proportional pressure may be used along with other clearing methods to clear material clogging the aspiration channel pathways and tubing of the surgical system.

In an embodiment of the present invention, the system may also mitigate post occlusion surge by applying just in time proportional pressure. The present invention may utilize the cross-connect functionality to more rapidly pressurize the aspiration line upon detection or prediction of a post occlusion surge, thereby reducing the pressure difference between the surgical field, the eye chamber for example, and aspiration line which may prevent, for example, a surge of fluid out of the anterior chamber of the eye.

The present invention may provide a phacoemulsification surgical system, comprising at least one pressure system comprising at least one irrigation line communicatively coupled to a first valve, at least one vacuum system comprising at least one aspiration line coupled to a second valve, at least one cassette removably attached to a surgical console and in communicatively coupled to the at least one irrigation line and the at least one aspiration line, and at least one cross-connection between the at least one pressure system and the at least one vacuum system, the at least one cross-connection configured to build proportional pressure between the at least one irrigation line and the at least one aspiration line.

The present invention may provide a surgical system including a surgical cassette, the surgical system comprising an aspiration line, an irrigation line, a pneumatic cross-connect proportional valve communicatively coupled between the aspiration line and irrigation line, the pneumatic cross-connect valve configured to vent and reflux the aspiration line, calibrate pressure and vacuum sensors of the surgical cassette, build proportional pressure or vacuum of the aspiration line and the irrigation line, and applying proportional pressure to clear obstructions of the aspiration line. The surgical system may further comprise at least one surgical console configured to house the pneumatic cross-connect proportional valve.

BRIEF DESCRIPTION OF THE DRAWINGS

This disclosure is illustrated by way of example and not by way of limitation in the accompanying figure(s). The figure(s) may, alone or in combination, illustrate one or more embodiments of the disclosure. Elements illustrated in the figure(s) are not necessarily drawn to scale. Reference labels may be repeated among the figures to indicate corresponding or analogous elements.

The detailed description makes reference to the accompanying figures in which.

DETAILED DESCRIPTION

It is to be understood that the figures and descriptions of the present invention have been simplified to illustrate elements that are relevant for a clear understanding of the present invention, while eliminating, for the purpose of clarity, many other elements found in typical surgical, and particularly optical surgical, apparatuses, systems, and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

Figure 1:
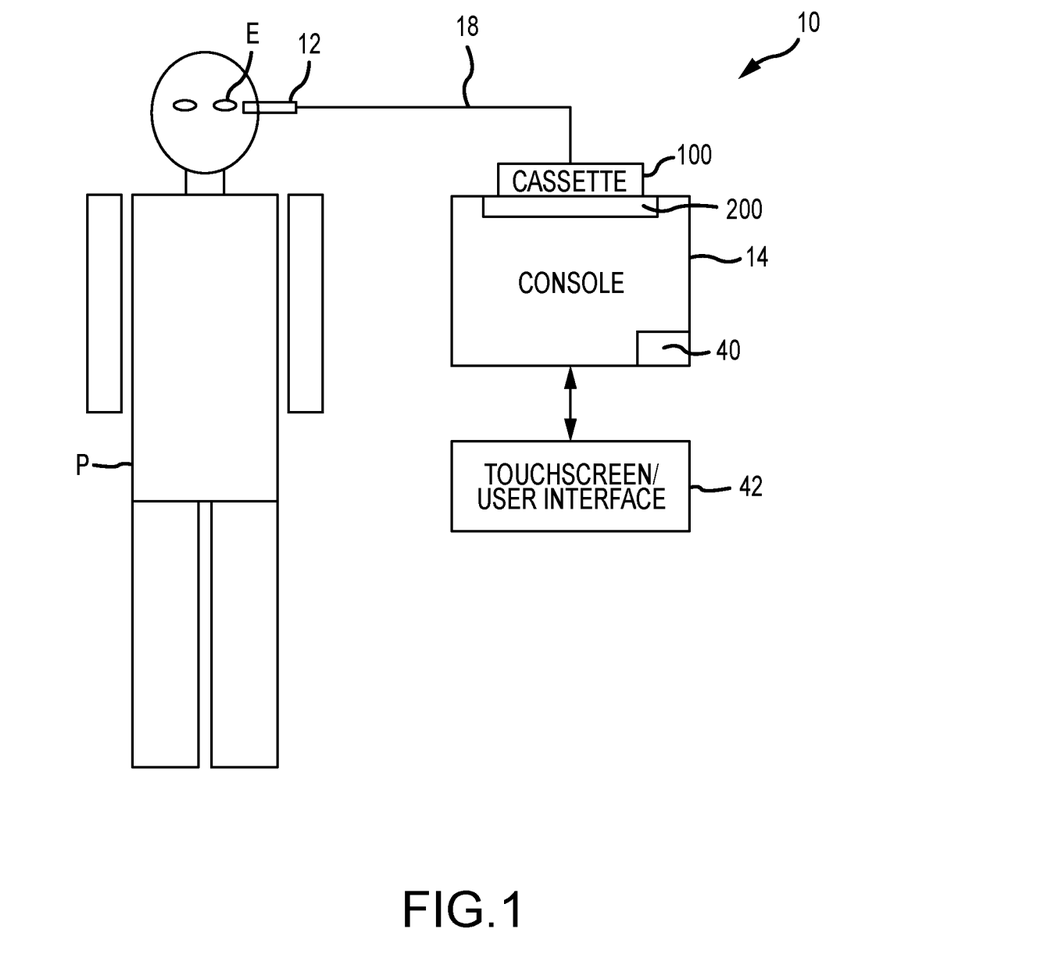
FIG. 1 schematically illustrates an eye treatment system in which a cassette couples an eye treatment probe with an eye treatment console.

Referring to FIG. 1, a system 10 for treating an eye E of a patient P generally includes an eye treatment probe handpiece 12 coupled to a console 14 by a cassette 100 mounted on the console via interface 200. Handpiece 12 may include a handle for manually manipulating and supporting an insertable probe tip. The probe tip has a distal end which is insertable into the eye, with one or more lumens in the probe tip allowing irrigation fluid to flow from the console 14 and/or cassette 100 into the eye. Aspiration fluid may also be withdrawn through a lumen of the probe tip, with the console 14 and cassette 100 generally including a vacuum aspiration source, a positive displacement aspiration pump, or both to help withdraw and control a flow of surgical fluids into and out of eye E. As the surgical fluids may include biological materials that should not be transferred between patients, cassette 100 will often be disposable or comprise a disposable (or alternatively, re-sterilizable) structure, with the surgical fluids being transmitted through conduits of the cassette that avoid direct contact in between those fluids and the components of console 14.

When a distal end of the probe tip of handpiece 12 is inserted into an eye E, for example, for removal of a lens of a patient with cataracts, an electrical conductor and/or pneumatic line (not shown) may supply energy from console 14 to an ultrasound transmitter of the handpiece, a cutter mechanism, or the like. Alternatively, the handpiece 12 may be configured as an irrigation/aspiration (IA) or vitrectomy handpiece. Also, the ultrasonic transmitter may be replaced by other means for emulsifying a lens, such as a high energy laser beam. The ultrasound energy from handpiece 12 helps to fragment the tissue of the lens, which can then be drawn into a port of the tip by aspiration flow. So as to balance the volume of material removed by the aspiration flow, an irrigation flow through handpiece 12 (or a separate probe structure) may also be provided, with both the aspiration and irrigations flows being controlled by console 14.

So as to avoid cross-contamination between patients and/or to avoid incurring excessive expenditures for each procedure, cassette 100 and its conduit 18 may be disposable. Alternatively, the conduit or tubing may be disposable, with the cassette body and/or other structures of the cassette being sterilizable. Regardless, the disposable components of the cassette are typically configured for use with a single patient and may not be suitable for sterilization. The cassette will interface with reusable (and often quite expensive) components of console 14, which may include one or more peristaltic pump rollers, a Venturi or other vacuum source, a controller 40, and the like.

Controller 40 may include an embedded microcontroller and/or many of the components common to a personal computer, such as a processor, data bus, a memory, input and/or output devices (including a touch screen user interface 42), and the like. Controller 40 will often include both hardware and software, with the software typically comprising machine readable code or programming instructions for implementing one, some, or all of the methods described herein. The code may be embodied by a tangible media such as a memory, a magnetic recording media, an optical recording media, or the like. Controller 40 may have (or be coupled to) a recording media reader, or the code may be transmitted to controller 40 by a network connection such as an internet, an intranet, an Ethernet, a wireless network, or the like. Along with programming code, controller 40 may include stored data for implementing the methods described herein and may generate and/or store data that records parameters corresponding to the treatment of one or more patients. Many components of console 14 may be found in or modified from known commercial phacoemulsification systems.

In a first embodiment, the use of a cross-connect valve, which may be a pneumatic cross-connect proportional valve, for example, may allow for the connecting of an irrigation channel to aspiration and vice versa to provide either pressurization or vacuum to the channel(s) as desired. The invention may provide the capability to build proportional pressure in an aspiration line to support fluidics features such as venting and reflux, for example. The present invention may provide an alternative method to vent and reflux an aspiration line. By way of non-limiting example, in vacuum mode, a proportional vacuum regulator may relieve vacuum in the aspiration line followed by allowing a proportional cross-connect valve to build desired pressure in the aspiration line thus pushing fluid out from the aspiration line at the distal end. In the flow mode, an aspiration line may be opened to a vacuum mode tank on the pneumatic side; the vacuum mode tank being at or near atmosphere pressure, thereby at least partially relieving any vacuum in the aspiration line. Similarly, a pneumatic proportional cross-connect valve may be engaged to build desired pressure in the aspiration line. Reflux may be achieved in an equivalent manner by allowing the proportional cross-connect pathway to further pressurize the aspiration line.

The use of an air-pneumatic system may provide a capability to build and relieve vacuum in an aspiration line as needed in vacuum mode aspiration. In one non-limiting example, a proportional vent valve may proportionally relieve vacuum in a vacuum tank and in turn the aspiration line as a function of a foot pedal treadle position. The foot pedal treadle position may for example, include at least a first position and second position. A similar functionality may apply when building vacuum in a vacuum tank as a function of foot pedal treadle travel from position 1 to position 2 in a linear mode.

To achieve venting, a fluidics subsystem may be utilized. The fluidics subsystem relieves vacuum in an aspiration line and gradually builds positive pressure based on a user-defined set point of venting strength. The proportional cross-connect valve provides capability to proportionally build pressure in the aspiration line up to set irrigation pressure to vent the aspiration channel. In one non-limiting example, in vacuum mode aspiration, when venting is activated, the fluidics subsystem may gradually relieve vacuum in the aspiration tank using a proportional vent valve and in turn vacuum is reduced at the distal end of the aspiration channel. Once the vacuum is relieved from the aspiration line, a cross-connect valve may be used to gradually pressurize the aspiration tank and in turn the distal end of the aspiration channel based on a desired venting strength.

In reflux, the fluidics subsystem, in one non-limiting example, refluxes contents of the aspiration line into an anterior chamber. The aforementioned proportional cross-connect valve may be utilized to gradually build positive pressure in the aspiration line up to the irrigation pressure. Contents of the aspiration line may then reflux to the anterior chamber as positive pressure is applied to the vacuum tank in the cassette. In this mode, the proportional cross-connect valve may pressurize the aspiration line up to a set irrigation pressure.

In a second embodiment, the use of a cross-connect valve, which may be a pneumatic cross-connect proportional valve, for example, may provide a capability to calibrate pressure/vacuum sensor in a surgical cassette. An eddy current probe may be mounted in the console and a communication compatible interface disc may be located in the cassette. The eddy current pressure/vacuum sensor may be calibrated for zero offset and gain parameters by applying a known pressure and vacuum measurement points using the air-pneumatic system. In one non-limiting example, when a cassette is captured in a system console, the system may begin a sensor calibration process through the interface disc. The irrigation and aspiration luers may also be connected.

The air-pneumatic system may create a series of known pressure set points using proportional main and vent valves. Such associated pressure may be applied to the pressurized irrigation tank in the cassette while the valve (e.g. rotary valve) is engaged to pressurize the irrigation tank so that it may be measured using the irrigation pressure sensor. A proportional cross-connect valve may be engaged such that regulated irrigation pressure from the air-pneumatic system is applied to the aspiration channel and the vacuum tank and measured using the aspiration pressure sensor in the cassette. Similarly, the aspiration valve (e.g. rotary valve) may be engaged to the vacuum tank. As a result, both pressure transducers in the cassette may measure a series of pressure set points being applied by the air-pneumatic system.

For vacuum, the air-pneumatic system may create a series of known vacuum set points using proportional main and vent valves. Such a vacuum may be applied to the vacuum tank in the cassette while the valve (e.g. rotary valve) may be engaged to the vacuum tank. This allows the known vacuum to be measured using the aspiration pressure sensor in the cassette. A proportional cross-connect valve may be engaged such that regulated vacuum from the air-pneumatic system is applied to the irrigation channel and irrigation tank and measured using the irrigation pressure sensor in the cassette while irrigation the valve (e.g. rotary valve) is engaged to the irrigation tank.

This method may allow the system to simultaneously calibrate irrigation and aspiration pressure sensors in the cassette for a series of known pressure and vacuum set points. This series of known pressure set points include measurement points between maximum and minimum allowed pressure in the system. Similar set points may be applied for the vacuum.

In a third embodiment, the use of a cross-connect valve, which may be a pneumatic cross-connect proportional valve, for example, may allow for the capability to build proportional pressure or vacuum in both the irrigation and aspiration lines to support the priming of the fluidics. Cassette calibration may be performed prior to priming. The primary objective of fluidics prime, in at least one instance, is to evacuate air pockets from irrigation and aspiration fluid pathways including respective tanks and bladders in the cassette.

In a first implementation example, a gravity irrigation and peristaltic aspiration fluid path is described. In this example, the air-pneumatic valves for irrigation and aspiration may be in a default off position. The irrigation and aspiration luers may be connected together. An IV pole may be raised to a predetermined position and the irrigation valve in the cassette may be opened to gravity. Fluid from the irrigation source may start flowing through the irrigation inlet, valve (e.g. rotary), irrigation pressure sensor and to an irrigation distal end. This may allow the system to confirm head height pressure as measured by the irrigation pressure sensor. On the aspiration circuit, the peristaltic pump may be rotated at predetermined rotations per minute thereby generating a certain flow rate which causes the fluid to travel through the aspiration tubing, aspiration pressure sensor, aspiration bladders and to the waste bag.

In a second implementation example, a pressurized irrigation and peristaltic aspiration fluid path is described. In this example, a proportional main valve and a vent valve may be engaged to maintain certain predetermined pressure(s) in the irrigation tank. The fluid may be drawn from the irrigation source using a peristaltic pump which is rotating at a predetermined rotation per unit of time, generally minutes. Fluid my then travel through the irrigation inlet, peristaltic bladders, and to the irrigation tank in the cassette. Once the fluid reaches a certain level in the tank, the irrigation valve (e.g. rotary valve) may be engaged to the tank so that fluid then flows through the valve and irrigation pressure sensor to the irrigation distal end. On the aspiration circuit, the peristaltic pump may be rotating at predetermined rotations per minute generating a certain flow rate which causes the fluid to travel through the aspiration tubing, aspiration pressure sensor, aspiration bladders, and to the waste bag. The air-pneumatic system may apply a series of pressure set points up to a maximum allowed.

In a third implementation example, a pressurized irrigation and vacuum aspiration fluid path is described. In this case, a proportional main valve and a vent valve may be engaged to maintain a certain predetermined pressure in the irrigation tank. The fluid may be drawn from the irrigation source using a peristaltic pump which is rotating at a predetermined rotation per minute. Fluid may travel through the irrigation inlet, peristaltic bladders, and to the irrigation tank in the cassette. Once the fluid reaches a certain level in the tank, the irrigation valve (e.g. rotary valve) may be engaged to the tank so that fluid flows through the valve and irrigation pressure sensor and to the irrigation distal end.

A proportional main valve and a vent valve may be engaged to maintain a certain predetermined vacuum in the aspiration tank. The aspiration valve (e.g. rotary valve) may be engaged to the tank so that fluid travels through the aspiration tubing, aspiration pressure sensor, and to the tank. Once the fluid reaches a certain level in the tank, the peristaltic pump may be rotated to evacuate fluid from the tank to a waste bag. The air-pneumatic system may apply a series of vacuum set points up to a maximum allowed amount of set points. The proposed solution is therefore enabled to support fluidics prime by utilizing the proportional cross-connect to build pressure or vacuum in both irrigation and aspiration lines when the lines are connected.

In a fourth embodiment, the use of a cross-connect valve, which may be a pneumatic cross-connect proportional valve, for example, may allow for the capability to clear clogging of an aspiration channel fluid pathways by applying proportional pressure.

In a fifth embodiment, the use of a cross-connect valve, which may be a pneumatic cross-connect proportional valve, for example, may allow for the capability to mitigate post occlusion surge by applying just in time proportional pressure. In one non-limiting example, in vacuum mode aspiration while the tip is occluded, the proportional vent valve can be used to gradually reduce vacuum in the aspiration line up to predetermined set point. Upon occlusion break, the vent valve relieves the remaining vacuum in the aspiration line followed by the cross-connect valve instantly applying an effective amount of positive pressure in the vacuum tank and in turn the aspiration line to mitigate the surge. Post occlusion surge occurs when a hand piece tip is blocked by a fragment or particulate of the cataractic lens. A blocked tip may cause a vacuum to build in the aspiration tubing. When the occlusion breaks, the stored energy in the tubing pulls fluid from the anterior chamber. The amount of volume that the aspiration tubing pulls depends on how much it had collapsed during the occlusion. By allowing the cross-connect valve to just-in-time apply a small effective amount of positive pressure in the aspiration line, the fluid movement from anterior chamber to aspiration tubing during the surge break may be reduced.

Figure 2A:
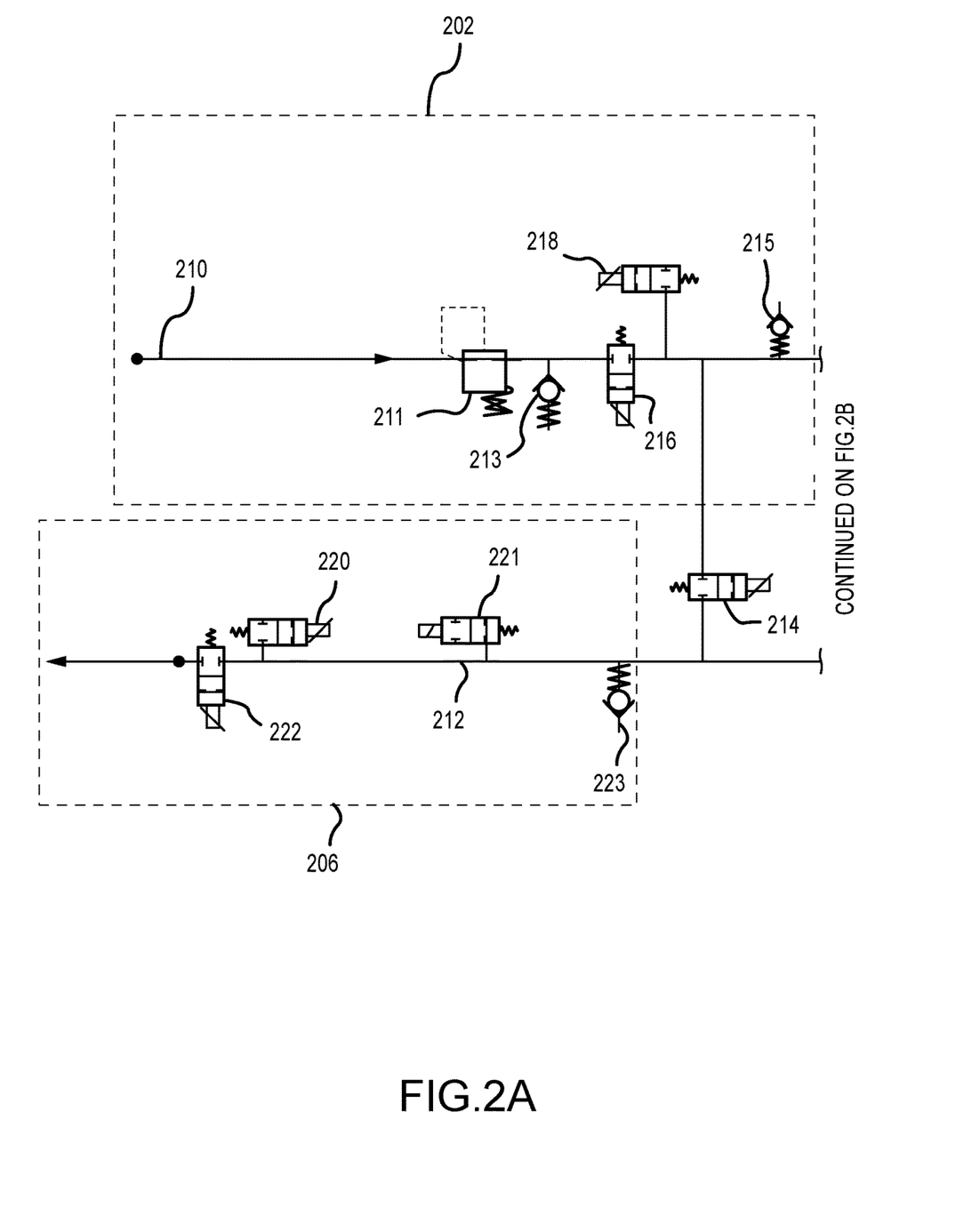
FIGS. 2A and 2B provide an exemplary diagram that illustrates a pneumatics connection of pressure and vacuum system with a key feature of cross-connection between two systems.
Figure 2B:
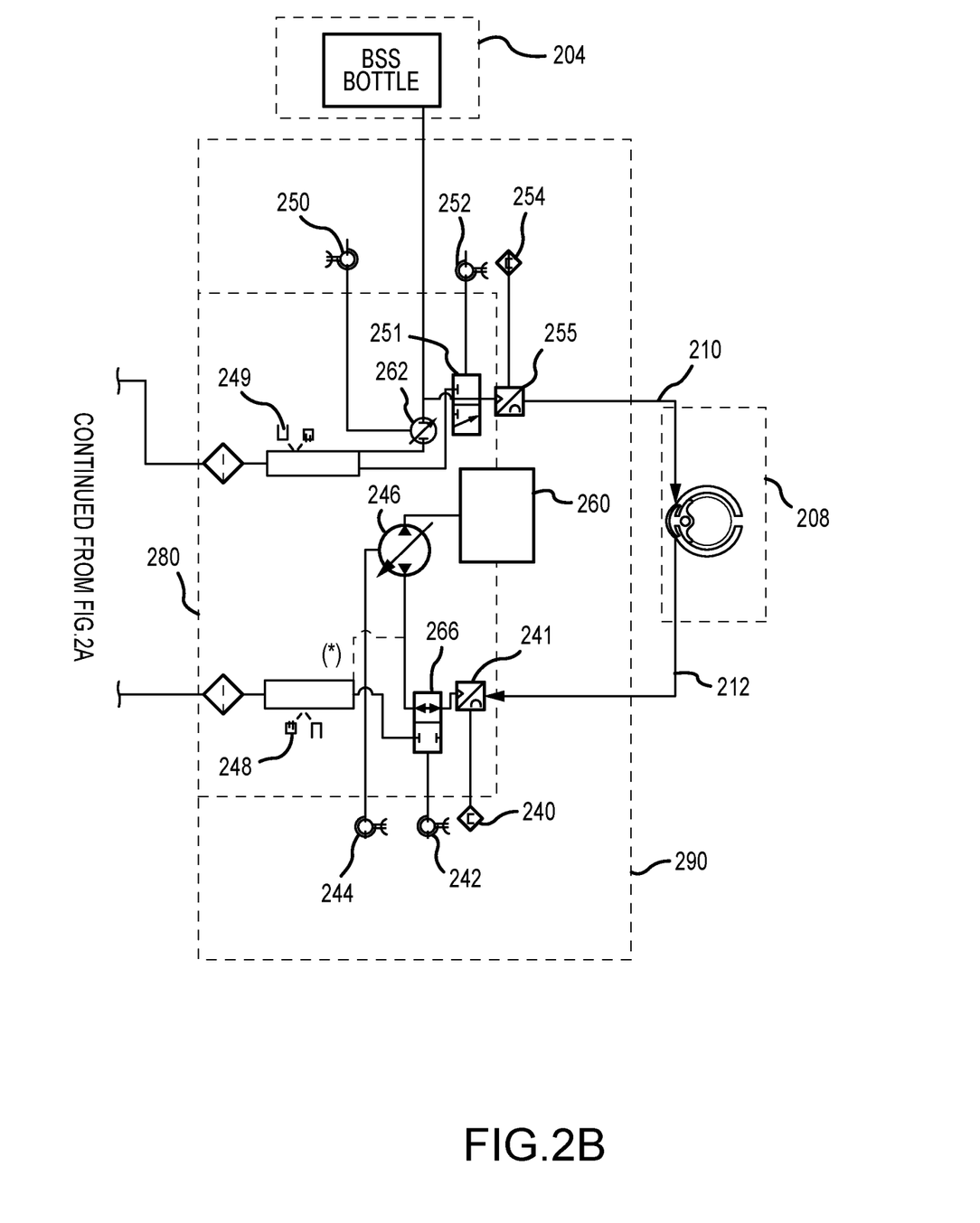

The diagram shown in FIGS. 2A and 2B illustrates pneumatics connection of a pressure and vacuum system having a cross-connection between the two systems. FIG. 2A includes an irrigation system 202 and a vacuum system 206 which are in communication with each other through at least one cross connect valve 214. The at least one cross connect valve 214 may be a proportional valve which may, for example, connect the irrigation system 202 to the vacuum system 206.

As illustrated in FIG. 2A, irrigation system 202 may include at least one irrigation line 210 communicatively coupled to at least one valve for the regulation of flow through the irrigation line 210. At least one of the valves may include vent valve 218 which may further be a proportional valve. Similarly, at least one of the valves may include a regulator valve 216, which may also be a proportional valve. Irrigation system 202 may also include air regulator 211 and at least one safety check valve 213. In addition, a sensor, such as sensor 215, may be in communication with irrigation line 210 to monitor pressure and/or fluid flow in line 210. The irrigation system 202 is preferably pressurized and may provide up to 120 mmHg of pressure for vent and reflux operations.

Aspiration system 206 may include at least one aspiration line 212 communicatively coupled to at least one valve for the regulation of flow through the aspiration line 212. At least one of the valves may include vent valve 221 which may further be a proportional valve. Similarly, at least one of the valves may include a regulator valve 220, which may also be a proportional and/or vent valve. An additional regulator valve 222 may be used and may in situated in-line with aspiration line 212. Aspiration system 206 may also a sensor, such as sensor 223, may be in communication with aspiration line 212 to monitor pressure and/or fluid flow in line 21.

As illustrated in FIG. 2B, a cassette 290 may be removably attached to a portion of surgical console 280 and may be in communication with aspiration line 212 and irrigation line 210. Cassette 290 may be in communication with pump 246 and associated drain bag 260, wherein the pump 246 may be a peristaltic pump, for example. Similarly, cassette 290 may be in communication with pump 262 and associated irrigation source 204, wherein the pump 262 may be a peristaltic pump, for example. Aspiration line 212 may be in communication with fluid level sensor 248 and at least one valve 266 proximate to cassette 290. The irrigation line 210 may be in communication with fluid level sensor 249 and at least on valve 251 proximate to cassette 290. Each fluid level sensor may be at least in part optical and may be of any suitable technology common to those skilled in the art.

Certain aspects of cassette 290 may at least partially control various aspects of the surgical console 280. For example, motor control 244 may control pump 246, motor control 242 may control valve 266, and sensor control 240 may control and/or read sensor 241. Similarly, motor control 250 may control pump 262, motor control 252 may control valve 251, and sensor control 254 may control and/or read sensor 255.

Aspiration line 212 and irrigation line 210 may be communicatively coupled through at least one proportional valve 214. Fluid communication between each of the lines and proportional valve 214 may occur at any position along each line and may, for example, occur prior to the distal end of each line. In an embodiment of the present invention, the at least one proportional valve 214 is located in the surgical console prior to either the aspiration line 212 or the irrigation line 210 enters cassette 210. In an embodiment of the present invention, the at least one proportional valve 214 is located outside the surgical console prior to either the aspiration line 212 or the irrigation line 210 terminating at the surgical site 208. The cross-connect provided by the at least one proportional valve 214 is normally closed, thereby isolating the pressure and vacuum pneumatic circuits.

Figure 3:
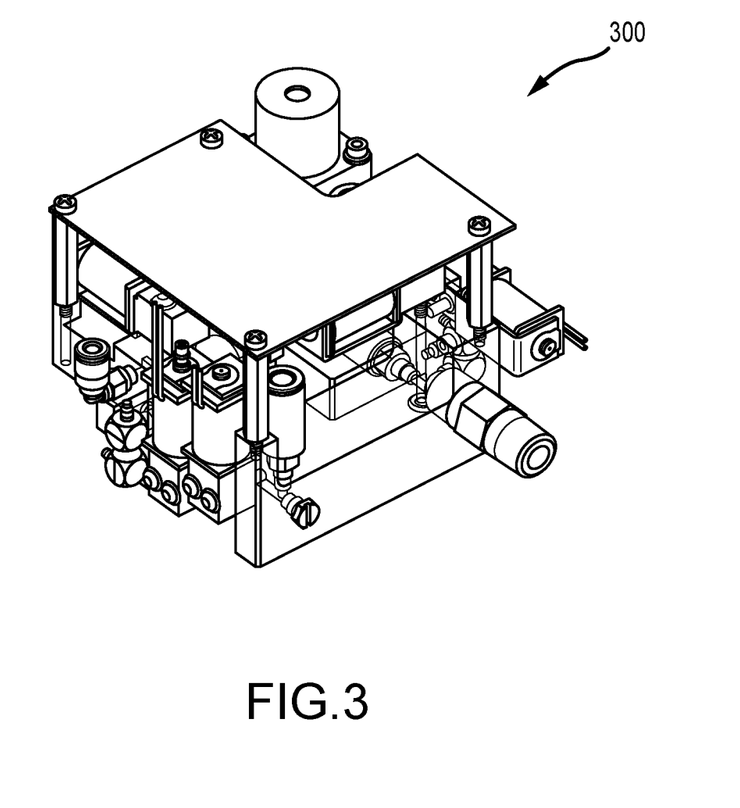
FIG. 3 is an exemplary diagram illustrates a design of a fluidics manifold assembly with cross-connect.

The diagram shown in FIG. 3 illustrates the present design of a fluidics manifold assembly 300 with cross-connect as described herein. The diagram shows an isometric view of the fluidics manifold assembly.

Those of skill in the art will appreciate that the herein described apparatuses, engines, devices, systems and methods are susceptible to various modifications and alternative constructions. There is no intention to limit the scope of the invention to the specific constructions described herein. Rather, the herein described systems and methods are intended to cover all modifications, alternative constructions, and equivalents falling within the scope and spirit of the disclosure, any appended claims and any equivalents thereto.

In the foregoing detailed description, it may be that various features are grouped together in individual embodiments for the purpose of brevity in the disclosure. This method of disclosure is not to be interpreted as reflecting an intention that any subsequently claimed embodiments require more features than are expressly recited.

Further, the descriptions of the disclosure are provided to enable any person skilled in the art to make or use the disclosed embodiments. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but rather is to be accorded the widest scope consistent with the principles and novel features disclosed herein.

The invention claimed is:

1. A phacoemulsification surgical system, comprising:
   at least one pressure system comprising at least one irrigation line communicatively coupled to a first valve;
   at least one vacuum system comprising at least one aspiration line coupled with a second valve;
   at least one cassette removably attached to a surgical console and communicatively coupled with the at least one irrigation line and the at least one aspiration line; and
   at least one cross-connection between the at least one pressure system and the at least one vacuum system, the at least one cross-connection configured to build proportional pressure between the at least one irrigation line and the at least one aspiration line.

2. The phacoemulsification surgical system of claim 1, wherein the at least one pressure system is configured to regulate flow through the at least one irrigation line via the first valve.

3. The phacoemulsification surgical system of claim 2, wherein the first valve is a vent valve.

4. The phacoemulsification surgical system of claim 2, wherein the first valve is a regulator valve.

5. The phacoemulsification surgical system of claim 1, wherein the at least one pressure system further comprises at least one air regulator.

6. The phacoemulsification surgical system of claim 1, wherein the at least one pressure system further comprises at least one safety check valve.

7. The phacoemulsification surgical system of claim 1, wherein the at least one pressure system further comprises at least one sensor communicatively coupled with the at least one irrigation line, the at least one sensor configured to:
   monitor pressure in the at least one irrigation line; or
   monitor fluid flow in the at least one irrigation line.

8. The phacoemulsification surgical system of claim 1, wherein the at least one vacuum system is configured to regulate flow through the at least one aspiration line via the second valve.

9. The phacoemulsification surgical system of claim 8, wherein the second valve is a vent valve.

10. The phacoemulsification surgical system of claim 8, wherein the second valve is a regulator valve.

11. The phacoemulsification surgical system of claim 1, wherein the at least one vacuum system further comprises at least one sensor communicatively coupled with the at least one aspiration line, the at least one sensor configured to:
    monitor pressure in the at least one aspiration line; or
    monitor fluid flow in the at least one aspiration line.

12. The phacoemulsification surgical system of claim 1, wherein the at least one cross-connection is a pneumatic cross-connect proportional valve.

13. The phacoemulsification surgical system of claim 1, wherein the cross-connection is configured to build and relieve vacuum in the at least one aspiration line during vacuum mode aspiration.

14. The phacoemulsification surgical system of claim 1, wherein the cross-connection is configured to:
    relieve vacuum in the at least one aspiration line;
    gradually build positive pressure based on a user set-point of venting strength; and
    set irrigation pressure thereby venting the at least one aspiration line.

15. The phacoemulsification surgical system of claim 1, wherein the cross-connection is configured to:
    gradually build positive pressure in the at least one aspiration line up to an irrigation pressure; and
    reflux contents of the at least one aspiration line into an anterior chamber in response to the positive pressure.

16. The phacoemulsification surgical system of claim 1, wherein the cross-connection is configured to:
    calibrate one or more sensors of the at least one cassette.

17. The phacoemulsification surgical system of claim 16, wherein the one or more sensors include at least one of a pressure sensor and a vacuum sensor.

18. The phacoemulsification surgical system of claim 1, wherein a negative pressure is applied to the at least one irrigation line.

19. The phacoemulsification surgical system of claim 1, wherein the proportional pressure is less than atmosphere.

* * * * *